United States Patent
Giribona et al.

(10) Patent No.: US 8,865,070 B2
(45) Date of Patent: Oct. 21, 2014

(54) MACHINE FOR THE PRODUCTION OF PHARMACEUTICAL PRODUCTS

(76) Inventors: Paolo Giribona, Trieste (IT); Walter Bianco, Trieste (IT); Michele Minisini, Trieste (IT); Garcia Gaspar de Viedma Santoro, Madrid (ES)

(*) Notice: Subject to any disclaimer, the term of this patent is extended or adjusted under 35 U.S.C. 154(b) by 596 days.

(21) Appl. No.: 12/870,875

(22) Filed: Aug. 30, 2010

(65) Prior Publication Data

US 2012/0048676 A1   Mar. 1, 2012

(51) Int. Cl.
| | |
|---|---|
| B65G 49/00 | (2006.01) |
| B65B 3/00 | (2006.01) |
| A61J 1/20 | (2006.01) |
| G01N 35/00 | (2006.01) |
| A61J 1/10 | (2006.01) |
| A61J 1/14 | (2006.01) |
| A61J 3/00 | (2006.01) |

(52) U.S. Cl.
CPC . B65B 3/003 (2013.01); A61J 1/20 (2013.01); G01N 35/0099 (2013.01); A61J 1/10 (2013.01); A61J 1/1462 (2013.01); A61J 1/2096 (2013.01); A61J 3/002 (2013.01)
USPC ....... 422/65; 422/63; 141/18; 141/2; 141/163

(58) Field of Classification Search
CPC ............ B65B 3/003; A61J 1/20; A61J 1/002; A61J 1/2096; A61J 1/1462; G01N 35/0099
See application file for complete search history.

(56) References Cited

U.S. PATENT DOCUMENTS

| | | | |
|---|---|---|---|
| 4,249,652 A * | 2/1981 | Brems .................... | 198/418.1 |
| 2006/0136095 A1 * | 6/2006 | Rob et al. .................... | 700/245 |

* cited by examiner

Primary Examiner — P. Kathryn Wright
(74) Attorney, Agent, or Firm — McCarter & English, LLP (57) ABSTRACT

A machine for the preparation of pharmaceutical products has a pocket conveyor, mobile along a loop-shaped path and provided with a plurality of pockets, each adapted to receive and withhold a respective container, and a transfer device for transferring the containers with a rectilinear motion between the respective pockets and at least one operating station for executing an operation on the containers themselves.

5 Claims, 13 Drawing Sheets

MACHINE FOR THE PRODUCTION OF PHARMACEUTICAL PRODUCTS

The present invention relates to a machine for the preparation of pharmaceutical products.

BACKGROUND OF THE INVENTION

A machine is known in the pharmaceutical product preparation field comprising a store for a plurality of containers, e.g. infusion bags, bottles and syringes; a dosing station for the preparation of a pharmaceutical product obtained by mixing, by means of a syringe, at least one pharmaceutical substance contained in a bottle and at least one diluent contained in an infusion bag; a weighing station of the bottles and/or of the infusion bags; and a robotized arm for gripping and transporting the containers.

The store, the dosing station, the weighing station and the robotized arm are accommodated within a sterile containment chamber limited by a protective casing provided with an access opening adapted to allow an operator to load and/or unload the various types of containers into/from the store itself.

Since the robotized gripping and transporting arm is normally used for transferring the various types of containers between the store, the weighing station, and the dosing station, the known machines for the preparation of pharmaceutical products have relatively long production cycles and relatively low productivity.

The known machines for the preparation of pharmaceutical products of the above-described type have the further drawback in that the loading and/or unloading operations of the store requires the machine to be stopped.

SUMMARY OF THE INVENTION

It is an object of the present invention to provide a machine for the preparation of pharmaceutical products which is free from the above-described drawbacks and which is simple and cost-effective to be implemented.

According to the present invention, there is provided a machine for the preparation of pharmaceutical products as claimed in the attached claims.

BRIEF DESCRIPTION OF THE DRAWINGS

The present invention will now be described with reference to the accompanying drawings, which illustrate a non-limitative embodiment thereof, in which:

FIG. 7b is a perspective view of a detail in FIG. 7a;

DETAILED DESCRIPTION OF THE INVENTION

Figure 1:
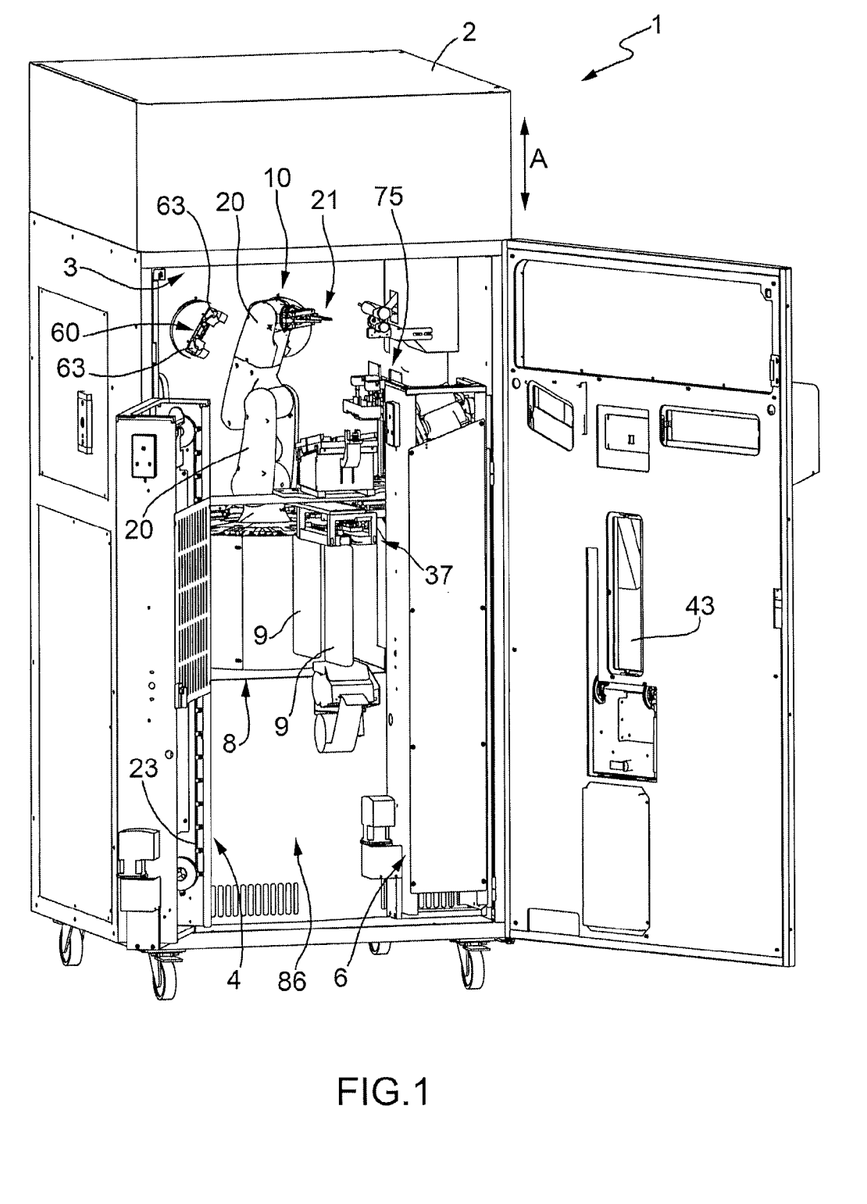
FIG. 1 is a diagrammatic perspective view, with parts removed for clarity, of a preferred embodiment of the machine according to the present invention.

With reference to FIG. 1, numeral 1 indicates as a whole a machine for the preparation of pharmaceutical products comprising a substantially parallelepiped containment box-like frame 2 defining an inner chamber 3, which is maintained in substantially sterile conditions by a pneumatic device of known type, shaped so as to feed a flow of sterile air through the chamber 3 and prevent the introduction of air from the external environment into the chamber 3.

The chamber 3 accommodates therein a store 4 for storing syringes 5; a store 6 for storing bottles 7; an annular store 8 for storing infusion bags 9; and a robotized gripping and transporting device 10 of the syringes 5 and/or of the bottles 7.

Each syringe 5 (FIG. 3) has a longitudinal axis 11, and comprises a cylinder 12 provided with an end flange 13 orthogonal to axis 11, a needle (not shown) coupled to the cylinder 12, a closing cap 14 mounted to protect the needle (not shown) from possible contaminations, and a piston 15, which is slidingly engaged in the cylinder 12, and is provided with an end head 16 perpendicular to axis 11.

Figure 5:
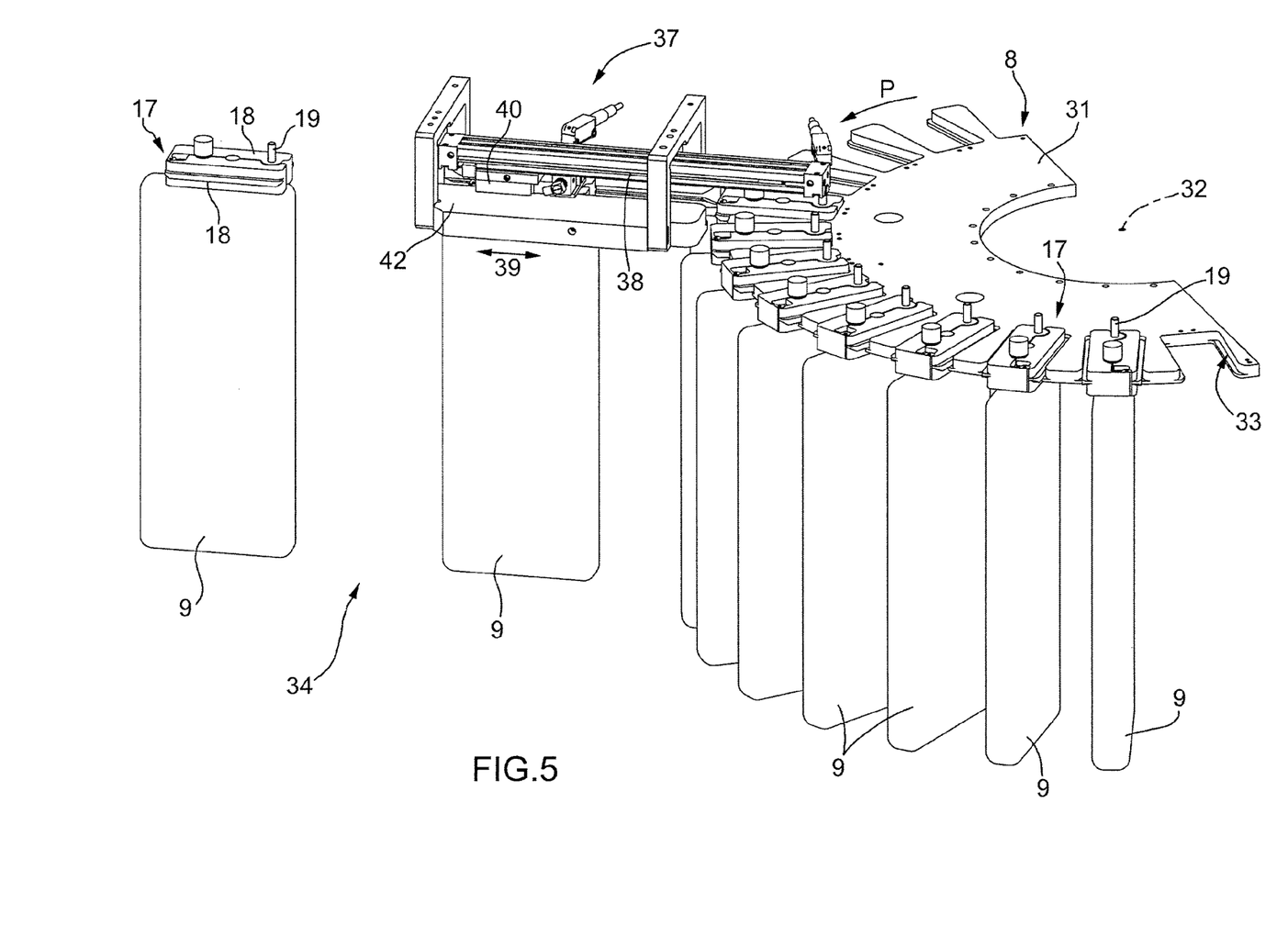
FIG. 5 is a diagrammatic perspective view, with parts removed for clarity, of a third detail of the machine in FIG. 1.

Each bag 9 is provided with an adapter member 17 of known type, which comprises two shaped jaws 18, mobile between a clamping position and a releasing position of an upper edge of the bag 9, and has a drawing pin 19 protruding upwards from one of the jaws 18 (FIG. 5).

Figure 3:
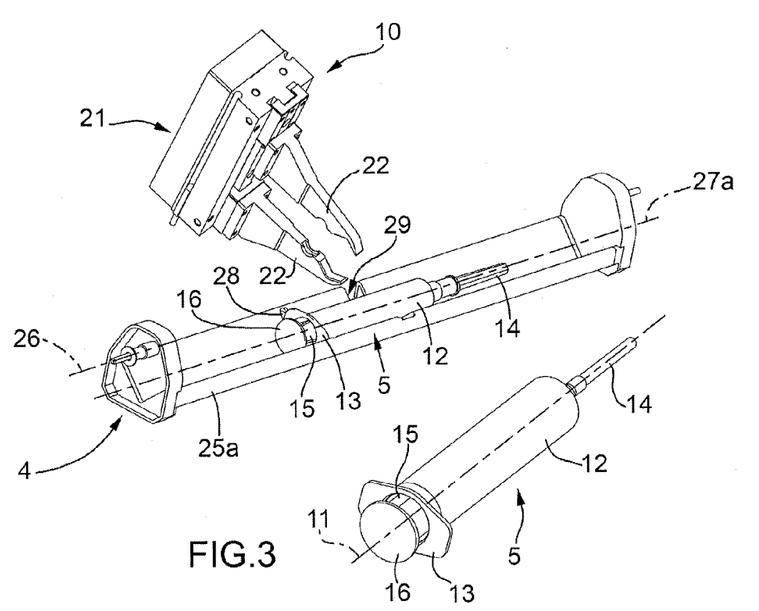
FIG. 3 is a diagrammatic perspective view, with parts removed for clarity, of a detail in FIG. 2.
Figure 4:
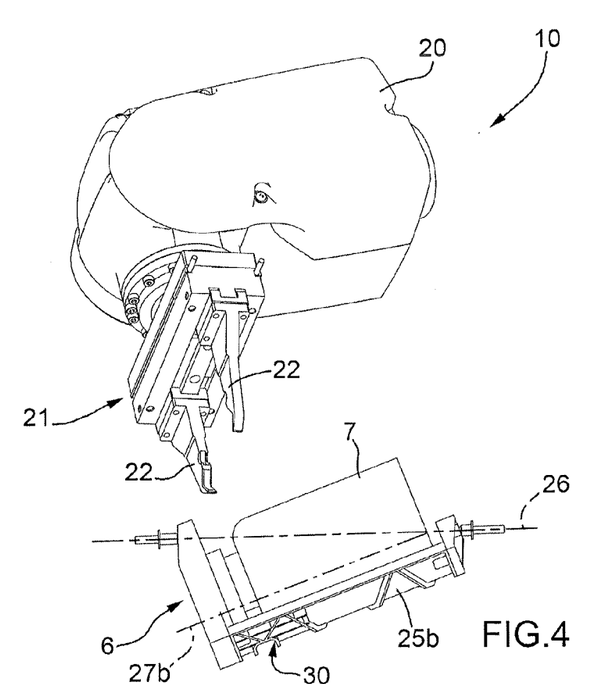
FIG. 4 is a diagrammatic perspective view, with parts removed for clarity, of a second detail of the machine in FIG. 1.

As shown in FIGS. 1, 3, and 4, the device 10 is mounted within the store 8, comprises a plurality of jointed arms 20 hinged to one another, and is provided with a gripping arm 21, which is mounted on the free end of the arms 20, and is defined by two jaws 22 mobile between a clamping position and a releasing position of a syringe 5 or a bottle 7.

Figure 2:
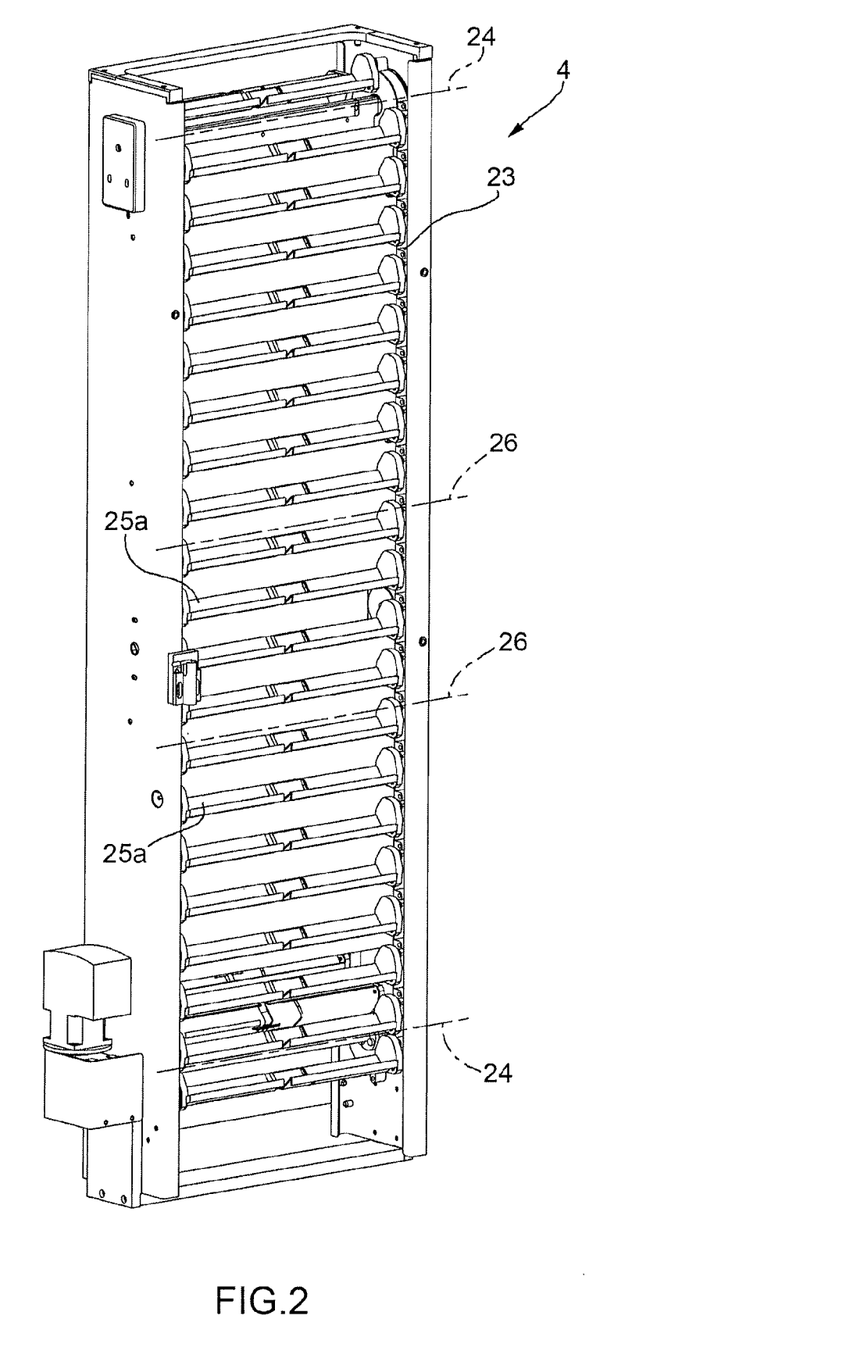
FIG. 2 is a diagrammatic perspective view, with parts removed for clarity, of a first detail of the machine in FIG. 1.

With reference to FIG. 2, each store 4, 6 comprises two reciprocally parallel belt conveyors 23, each of which extends in a substantially vertical direction A, faces the other conveyor 23, and is looped about a pair of pulleys (not shown), which are coaxial with the pulleys (not shown) of the other conveyor 23, and are mounted so as to intermittently rotate about respective rotation axis 24 parallel to one another and transversal to direction A.

Each store 4, 6 further comprises a plurality of transport cradles 25, which extend between the conveyors 23, are coupled to the conveyors 23 to oscillate, with respect to conveyors 23, about respective fulcrum axes 26 parallel to one another and to axes 24, and are uniformly distributed along the conveyors 23 themselves.

As shown in FIG. 3, each cradle 25 of the store 4 (hereinafter indicated by numeral 25a) has a substantially V-shaped transversal section, is arranged with a longitudinal axis 27a thereof parallel to axes 24, 26, is provided with a first slot 28 adapted to receive the flange 13 of a syringe 5 to guarantee the correct longitudinal positioning of the syringe 5 in the cradle 25a, and further has a second slot 29 adapted to be engaged by the jaws 22 to allow the device 10 to pick the syringe 5 from the cradle 25a itself.

With reference to FIG. 4, each cradle 25 of the store 6 (hereinafter indicated by numeral 25b) has a substantially V-shaped transversal section, is arranged with a longitudinal axis 27b thereof inclined with respect to axis 24, 26, and is provided with a slot 30, which is obtained near the lower end of the cradle 25b, allows to correctly position a bottle 7 with its concavity facing downwards, and allows the jaws 22 to pick the bottle 7 itself.

Since each store 4, 6 extends through a loading station obtained through the frame 2 to allow the operator to load the syringes 5 or bottles 7 into the respective cradles 25a, 25b, and through a single picking station, where the syringes 5 or the bottles 7 are picked from the respective cradles 25a, 25b by the device 10, the device 10 is relatively simple and cost-effective. Furthermore, the loading and unloading of the syringes 5 and of the bottles 7 in, and respectively from, the respective cradles 25a, 25b do not require the machine 1 to be stopped at all.

Figure 6:
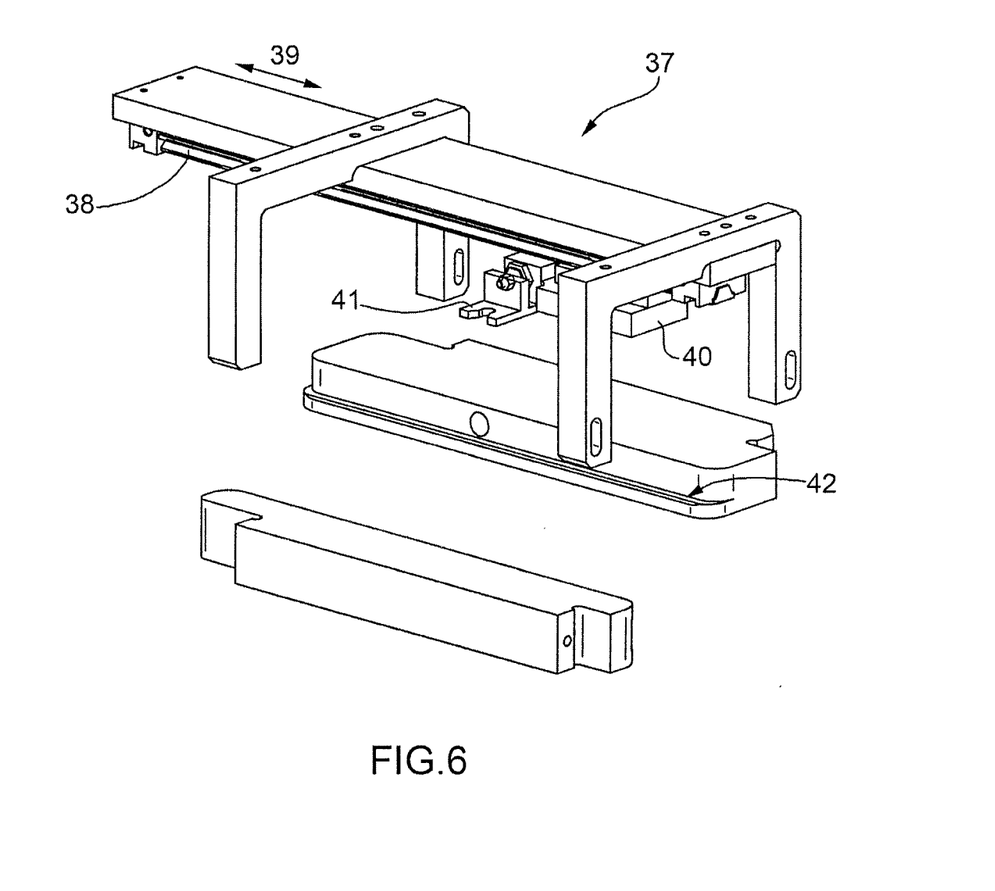
FIG. 6 is a diagrammatic perspective view, with parts removed for clarity, of a detail in FIG. 5.

As shown in FIGS. 5 and 6, the store 8 comprises an annular, star-shaped wheel 31, which extends about the device 10, is mounted to rotate intermittently, with respect to the frame 2 and under the bias of an actuating device (known and not shown), about a substantially vertical rotation axis 32, and has a plurality of pockets 33, which are obtained along a peripheral edge of the wheel 31, open radially outwards and are each adapted to receive and withhold a respective infusion bag 9.

The pockets 33 are fed by the wheel 31 about axis 32 and along a circular path P extending through a loading and unloading station 34 of the bags 9 into, and respectively from, the store 8, a weighing station 35 of the bags 9, and a dosing station 36 for injecting a predetermined amount of pharmaceutical into the bags 9 themselves.

Each station 34, 35, 36 is provided with a linear transfer device 37 comprising a rectilinear guide 38 parallel to a horizontal direction 39 transversal to axis 32, a slide 40 slidingly coupled to the guide 38 to perform rectilinear movements along the guide 38 in direction 39, and a gripping fork 41 slidingly coupled to the slide 40 to move, with respect to the slide 40 and transversally to direction 39, between a coupling position and a releasing position of the pin 19 of a respective adapter member 17.

The device 37 from station 34 cooperates with a guide 42, which is parallel to the respective guide 38, is radially aligned with the pocket 33 arranged each time in station 34 to be slidingly engaged by the member 17 of a respective bag 9, and extends between the store 8 and an opening 43 obtained through the frame 2 to allow an operator to load the bags 9 on the guide 42 and to pick the bags 9 from the guide 42 itself.

Figure 7A:
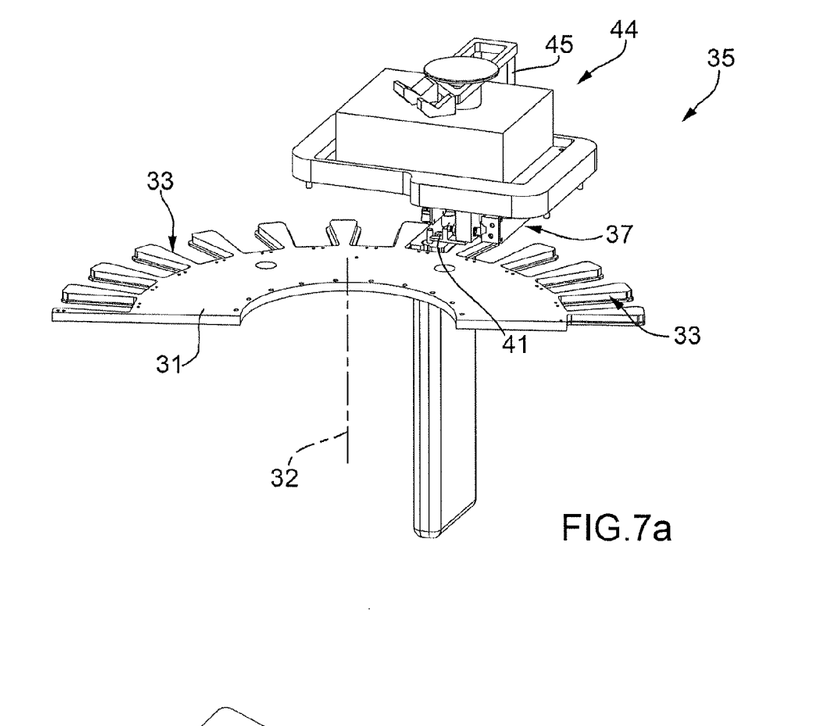
FIG. 7a is a diagrammatic perspective view, with parts removed for clarity, of a fourth detail of the machine in FIG. 1.
Figure 7B:
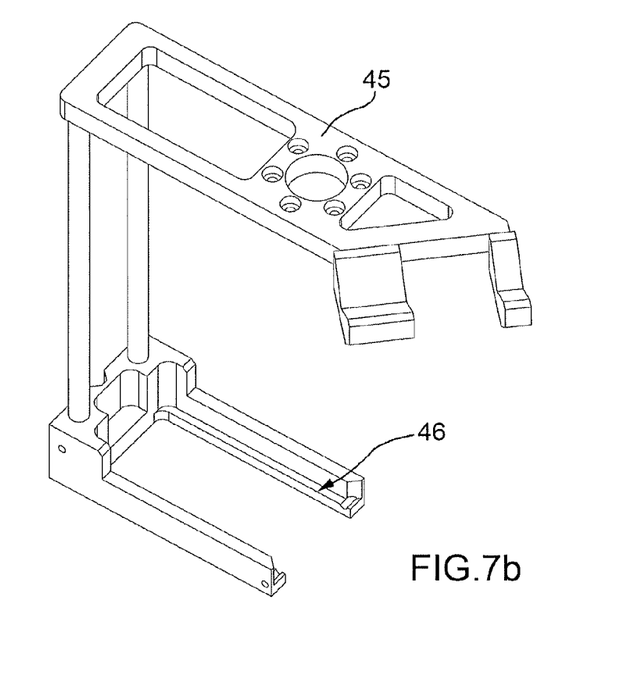

With reference to FIGS. 7a and 7b, device 37 of station 35 cooperates with a weighing device 44 comprising a supporting mobile member 45, which is coupled in known manner to a fixed part of the device 44 to move vertically under the weight of the bags 9, is fork-shaped and defines a guide 46 radially aligned with the pocket 33 arranged on each time in station 35 to be slidingly engaged by the member 17 of a respective bag 9.

The device 37 of station 36 cooperates with a guide (not shown), which is parallel to the respective guide 38, is radially aligned with the pocket 33 arranged each time in station 36 to be slidingly engaged by the member 17 of a respective bag 9, and is adapted to stop the bag 9 itself underneath a syringe 5, which is transferred from the device 10 between the store 4 and a gripping and actuating assembly 47 of the syringe 5 itself.

Figure 8:
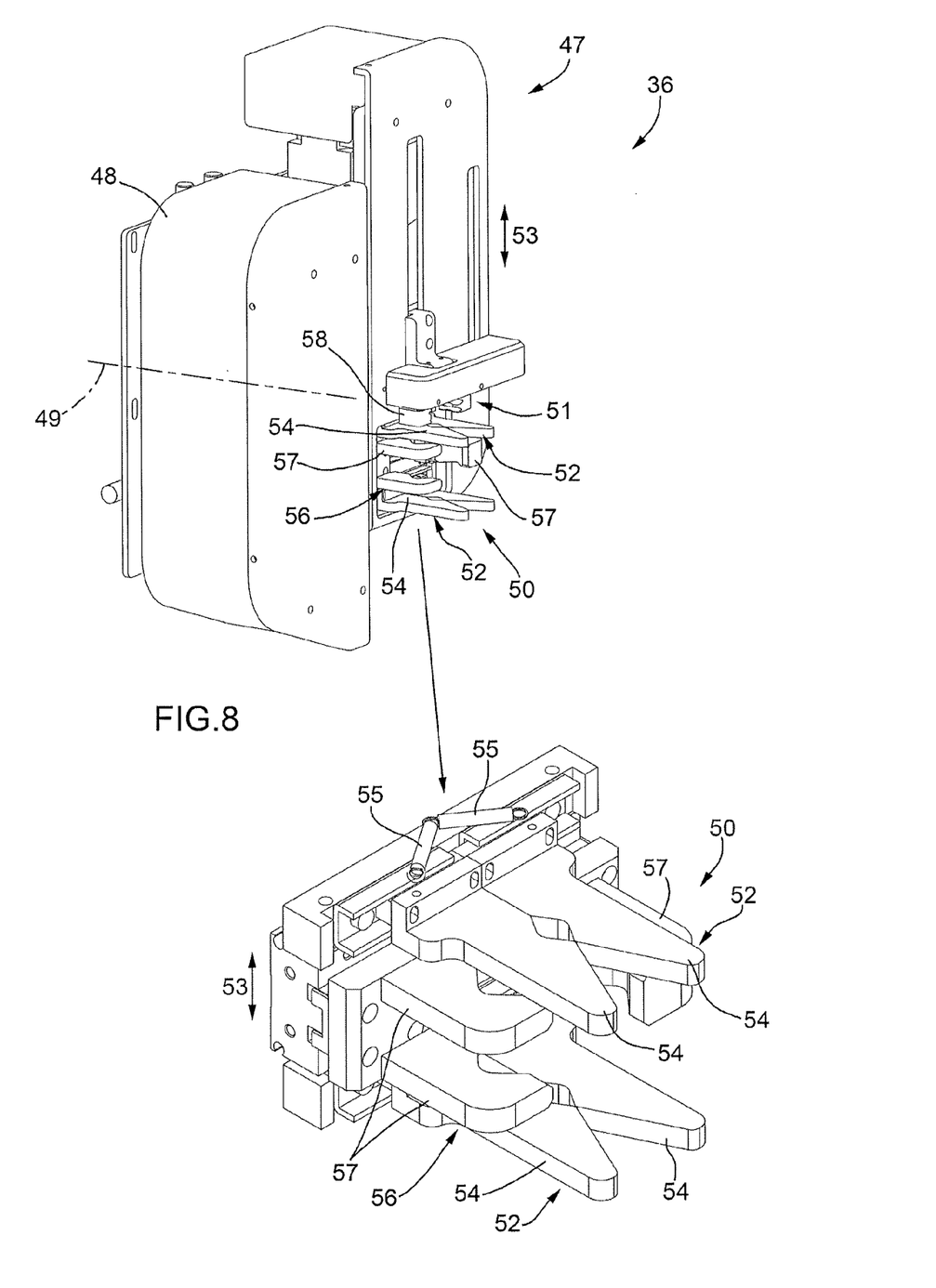
FIG. 8 is a schematic perspective view, with parts enlarged and parts removed for clarity, of a fifth detail of the machine in FIG. 1.
Figure 9:
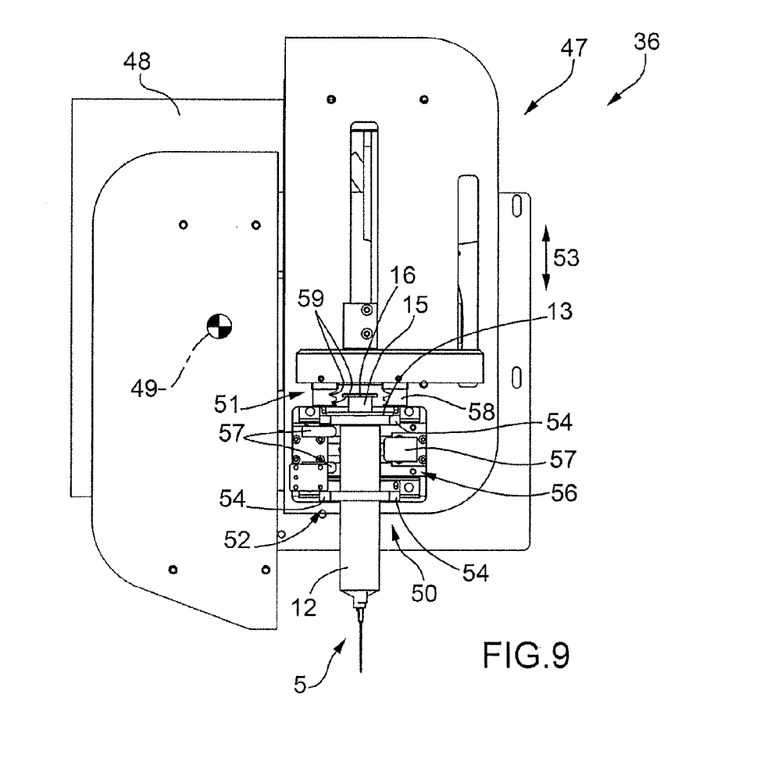
FIG. 9 is a diagrammatic front view, with parts removed for clarity, of the detail in FIG. 8.

As shown in FIGS. 8 and 9, the assembly 47 comprises a supporting block 48, which is mounted to rotate about a horizontal rotation axis 49 transversal to axis 32, and supports a gripping device 50 of the cylinder 12 and a gripping device 51 of the piston 15.

The device 50 comprises two grippers 52, which are reciprocally aligned in a direction 53, the orientation of which depends on the position of the block 48 about axis 49, and each comprise two respective jaws 54, which are slidingly coupled to the block 48 to move, with respect to the block 48 itself, transversally to direction 53, and are normally maintained in a clamping position of the cylinder 12 by respective springs 55 arranged between the block 48 and the jaws 54 and loaded so as to allow the axial movement of the syringe 5 through the grippers 52.

The device 50 further comprises an intermediate gripper 56, which extends between the grippers 52, and comprises, in turn, two jaws 57 slidingly coupled to the block 48 to move with respect to the block 48 and under the bias of an actuating device (known and not shown), transversally to direction 53 between a clamping position and a releasing position of the cylinder 12 of a syringe 5.

With regards to the above, it is worth noting that the jaws 57 are shaped so as to allow one of the jaws 57 to be inserted inside the other jaw 57 and also to clamp syringes 5 of relatively small diameter.

The device 51 comprises two jaws 58, which are slidingly coupled to the block 48 to move with respect to the block 48 and under the bias of an actuating device (known and not shown), transversally to direction 53 between a clamping position and a releasing position of the head 16 of a syringe 5, and are further slidingly coupled to the block 48 to perform rectilinear movements in direction 53 itself with respect to the block 48 and under the bias of an actuating device (known and not shown). Each jaw 58 has a plurality of grooves 59 (two grooves 59, in the case in point) superimposed on one another in direction 53 to allow the device 51 to receive and withhold the heads 16 of syringes 5 of different size.

The operation of the assembly 47 will now be described starting from an instant in which the jaws 57 and the jaws 58 are arranged in their releasing positions and the syringe 5 is inserted by the device 10 within the jaws 54 against the bias of the springs 55.

Once the syringe 5 is inserted within the grippers 52, the jaws 58 are firstly closed over the head 16 and then lowered in direction 53 so as to move the syringe 5 through the grippers 52, arrange the flange 13 in contact with the upper gripper 52 and, possibly, push the piston 15 fully into the cylinder 12.

The operating sequence shown above allows to correctly position the syringe 5 in direction 53 and guarantees a correct, constant positioning of all syringe 5 regardless of the size thereof, of the initial position of the pistons 15 along the respective cylinders 12, and of the initial axial and angular positions of the syringes 5 in the grippers 52.

Finally, the jaws 57 are moved in the clamping position of the syringe 5 within the assembly 47, and the jaws 58 are moved to the clamping position of the head 16 for controlling the movement of the piston 15 during the steps of aspirating and injecting of the pharmaceutical.

Figure 10:
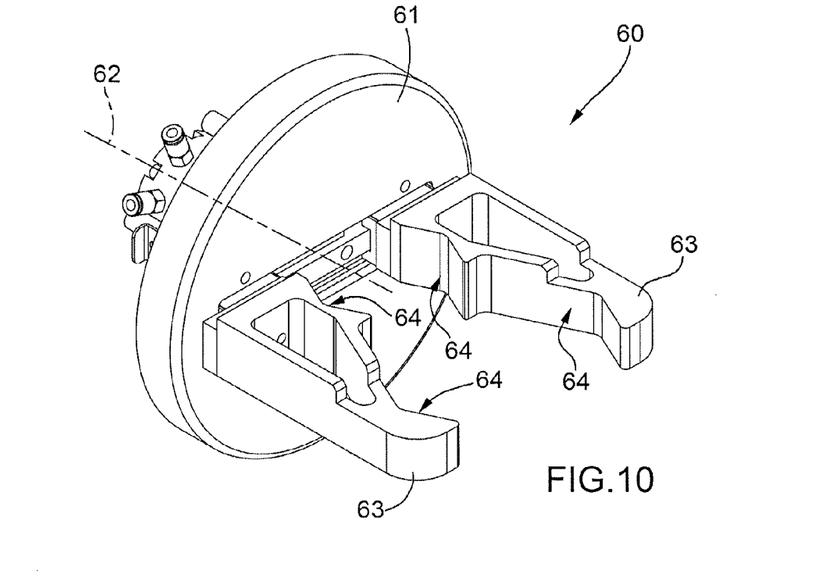
FIG. 10 is a diagrammatic perspective view, with parts removed for clarity, of a sixth detail of the machine in FIG. 1.

With reference to FIG. 10, the machine 1 further comprises a mixer device 60 for mixing a lyophilized or powder pharmaceutical and a diluent contained in a bottle 7 to one another.

The device 60 comprises a rotating plate 61, which is mounted to alternatively rotate about a substantially horizontal rotation axis 62, and is provided with a pair of jaws 63 coupled in known manner to the plate 61 to move, with respect to the plate 61, transversally to the axis 62, between a clamping position and a releasing position of a bottle 7. Each jaw 63 is shaped so as to display, in the case in point, a pair of seats 64, which cooperate with corresponding seats 64 of the other jaw 63 to allow the jaws 63 to withhold bottles 7 of different size.

Figure 11:
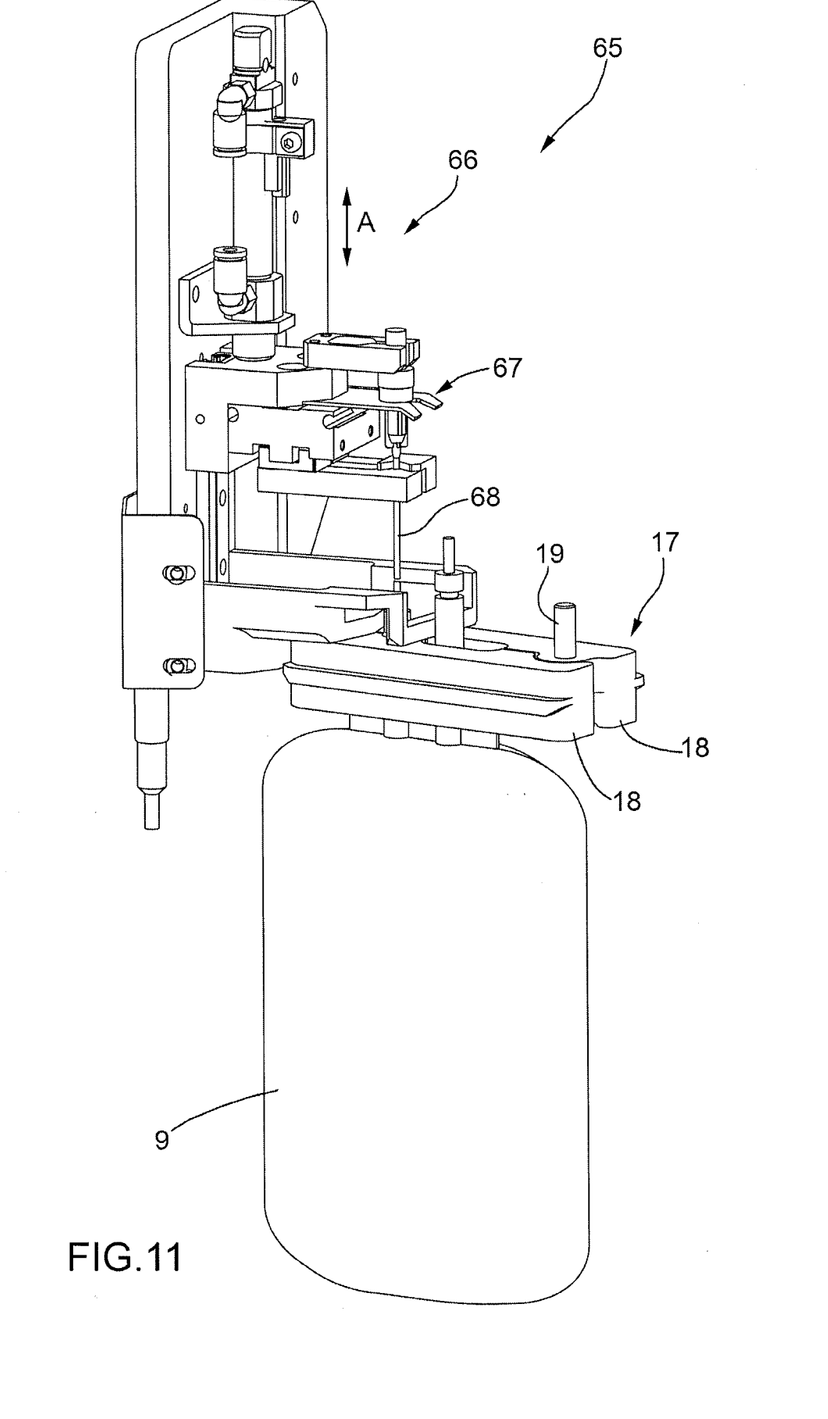
FIG. 11 is a diagrammatic perspective view, with parts removed for clarity, of a seventh detail of the machine in FIG. 1.
Figure 12:
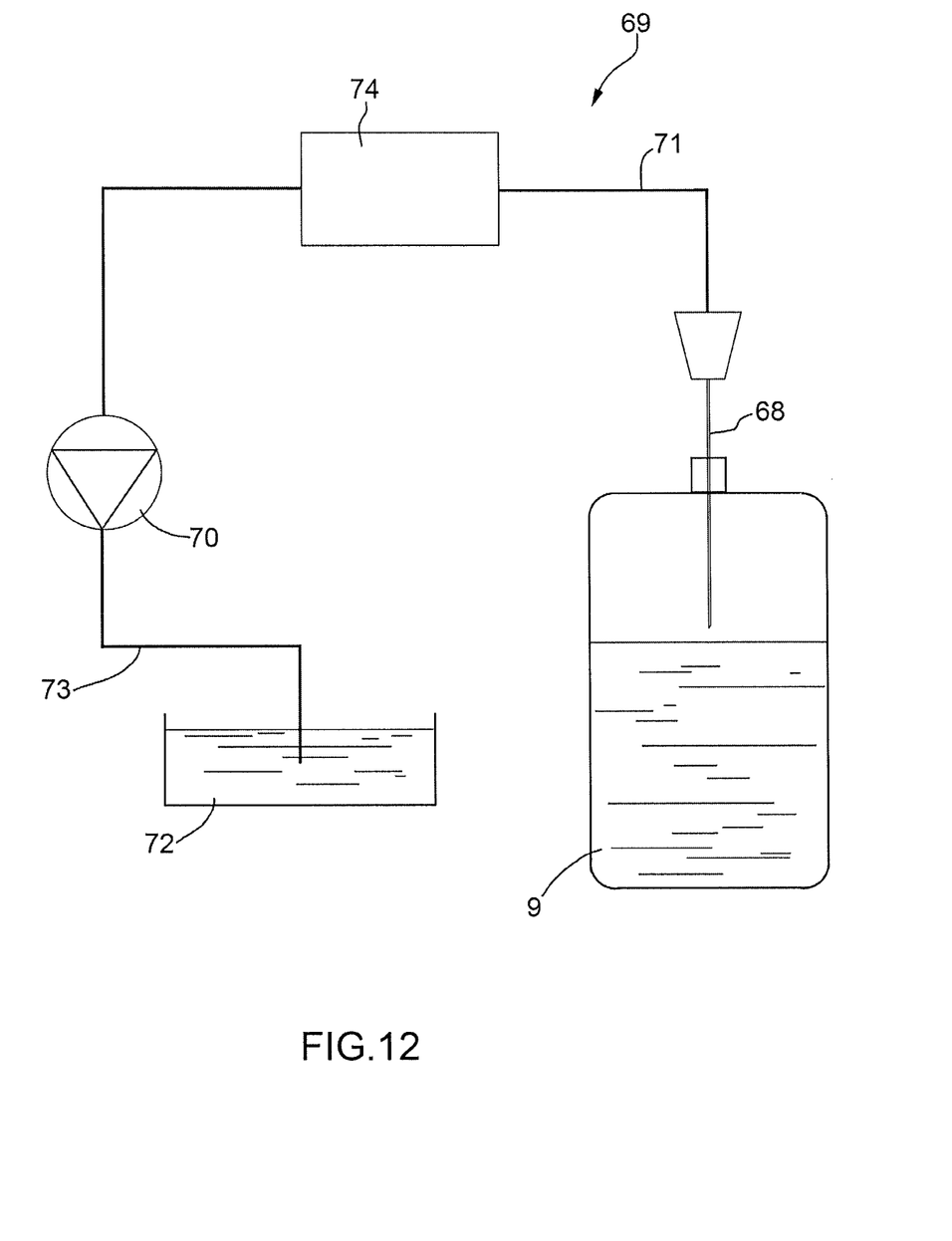
FIG. 12 diagrammatically shows the operating principle of the detail in FIG. 11.

As shown in FIGS. 11 and 12, the path P further extends through a picking station 65 of a predetermined amount of liquid from the bags 9. The picking of the liquid from bag 9 is necessary when the total weight of the pharmaceutical and of the diluent contained in the bag 9 after having injected the pharmaceutical needs to be equal to a determined value lower than the weight of the diluent initially contained in the bag 9 itself alone.

The station 65 has an aspiration assembly 66 comprising a gripping device 67 adapted to receive and withhold an extraction needle 68, which is connected to a hydraulic aspiration circuit 69, is transferred by the device 10 in the device 67 after having been separated from a protective cap thereof (known and not shown), and is moved by the device 67 in direction A between a raised resting position, in which the needle 68 is arranged outside the bag 9, and a lowered operating position, in which the needle 68 protrudes within the bag 9 over the diluent contained in the bag 9 itself.

The circuit 69 comprises an extraction pump 70, a peristaltic pump in the case in point, having an inlet hydraulically connected to the needle 68 by means of a first pipe 71, and an outlet hydraulically connected to a collection reservoir 72 of the diluent picked from the bags 9 by means of a second pipe 73.

Since the bags 9 contain a determined amount of air, the pipe 71 is provided with a flow sensor 74, a capacitance sensor in the case in point, which allows to discriminate between the passage of air and of liquid along the pipe 71, and thus correctly calculate the volume of liquid aspirated from the bags 9 by means of the pump 70. In other words, the volume of liquid aspirated from the bags 9 is calculated only starting from the instant in which the sensor 74 detects the passage of liquid along the pipe 71.

Figure 13A:
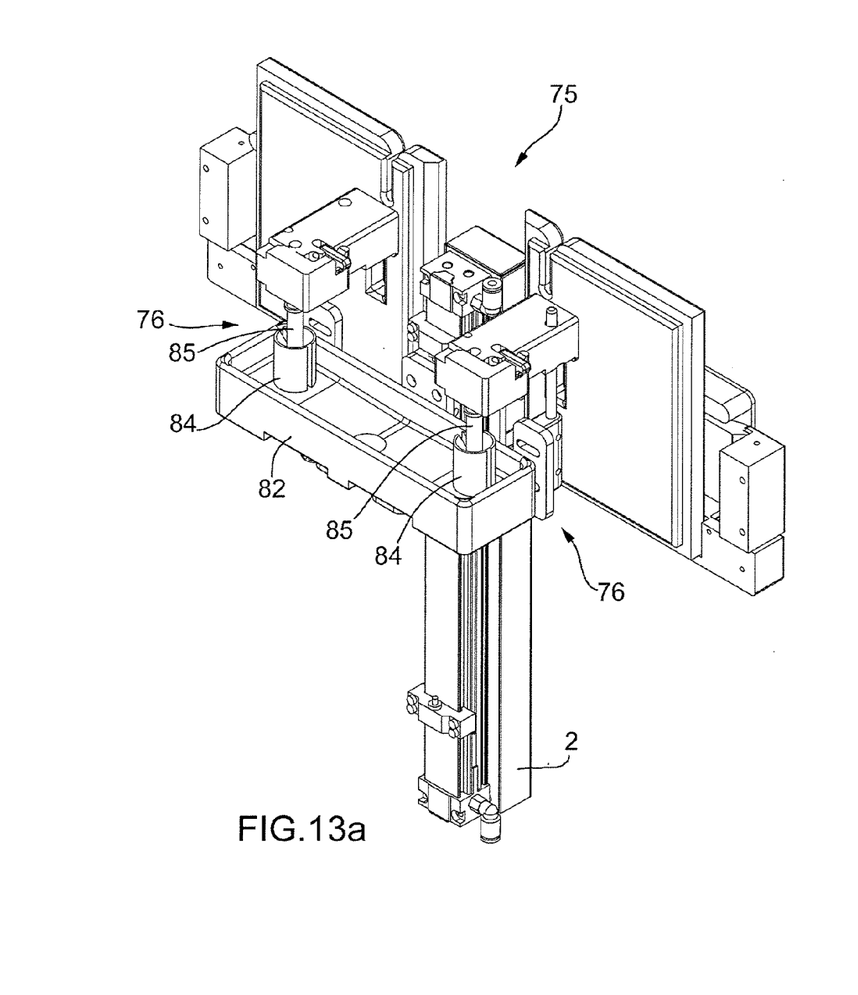
FIGS. 13a and 13b are diagrammatic perspective views, with parts removed for clarity, of an eighth detail of the system in FIG. 1 shown in two different operating positions.
Figure 13B:
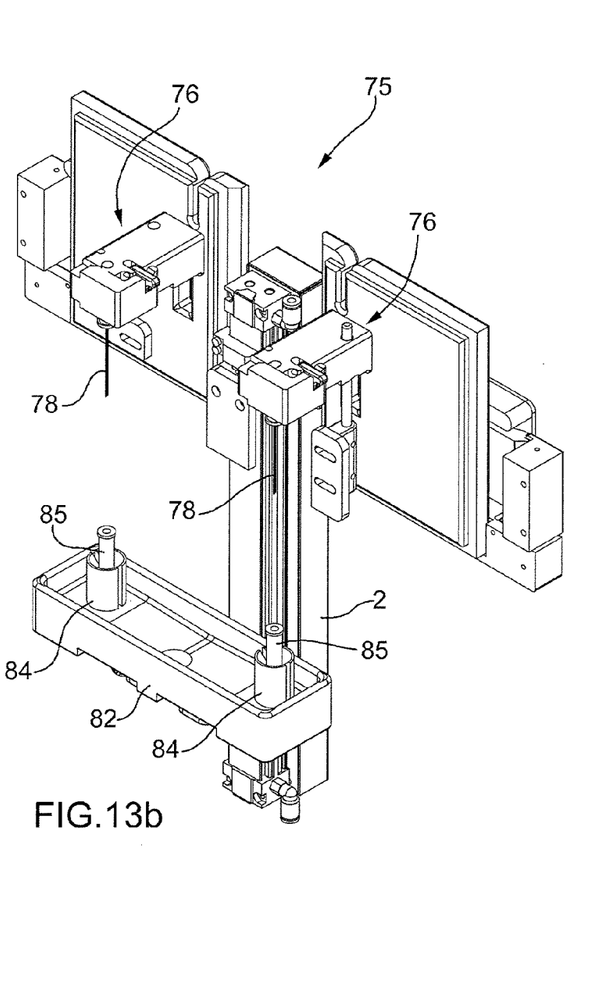
Figure 14:
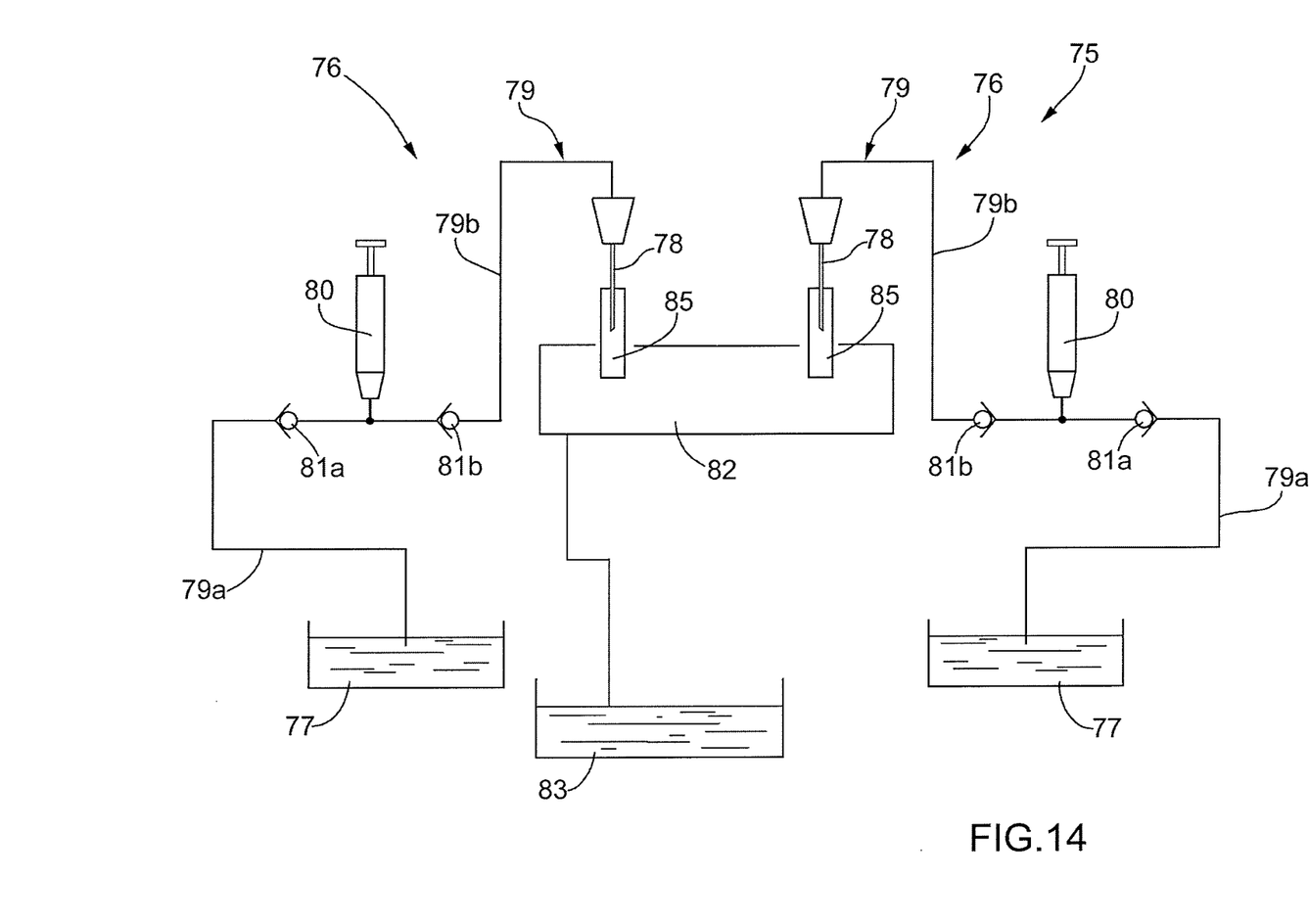
FIG. 14 diagrammatically shows the operating principle of the detail in FIG. 13.

With reference to FIGS. 13a, 13b and 14, the machine 1 further comprises a feeding device 75 for feeding a diluent into a bottle 7 containing a lyophilized or powder pharmaceutical.

The device 75 comprises feeding assemblies 76, two in the case in point, each of which comprises, in turn, a feeding reservoir 77 (e.g. a bag 9) for the diluent; a feeding needle 78 coupled to the frame 2 and hydraulically connected to the reservoir 77 by means of a pipe 79; and a pumping device defined, in the case in point, by a syringe 80, which is connected to an intermediate point of the pipe 79, and is actuated in known manner to aspirate a predetermined amount of diluent from the reservoir 77 and to feed the diluent itself into the bottle 7.

The connection between the pipe 79 and the syringe 80 divides the pipe 79 into two segments 79a, 79b, which are arranged in sequence and in this order between the reservoir 77 and the needle 78, and which are provided with respective check valves 81a, 81b, of which valve 81a avoids the flow back of diluent into segment 79a when diluent is fed to the needle 78, and valve 81b avoids the flow back of diluent from segment 79b when the diluent is aspirated from the reservoir 77.

The device 75 further comprises a collection reservoir 82, which extends underneath the needles 78, is coupled in known manner to the frame 2 to move with respect to the frame 2, in direction A between a lowered resting position (FIG. 13b) and an operating raised position (FIG. 13a), and is hydraulically connected to a collection manifold 83 of the diluent. The reservoir 82 further displays a pair of tubes 84, each of which protrudes upwards from a bottom wall of the reservoir 82, is substantially coaxial to the respective needle 78, and accommodates therein a protective cap 85 of the needle 78 itself arranged in the tube 84 with the concavity facing upwards.

In use, the reservoir 82 is moved, with the caps 85 of the needles 78, to its lowered resting position to allow inserting two bottles 7 underneath the needles 78 and feeding the diluent into the bottles 7 themselves.

When they are extracted from the respective bottles 7 the needles 78 may have residues of the lyophilized or powder pharmaceutical, and for this reason at the end of each injection operating cycle of the feeding device 75, the reservoir 82 is moved into its raised operating position so as to fit the caps 85 on the respective needles 78, and the syringes 80 are actuated to allow to wash the needles 78 with the diluent contained in the reservoirs 77.

The diluent fed through the needles 78 flows firstly into the respective caps 85 and thus into the reservoir 82 and into the manifold 83. With this regard, it is worth noting that:

the amount of diluent used to wash the needles 78 also allows to wash the caps 85;

the caps 85 are, like the needles 78, initially sterile and may therefore be used to wash the respective needles 78 at the end of each programmed injection operating cycles in a working session of the machine 1; and the conclusion of the working session of the machine 1 requires only the replacement of needles 78 and of the respective caps 85 and does not require the sterilization of the reservoir 82.

Figure 15:
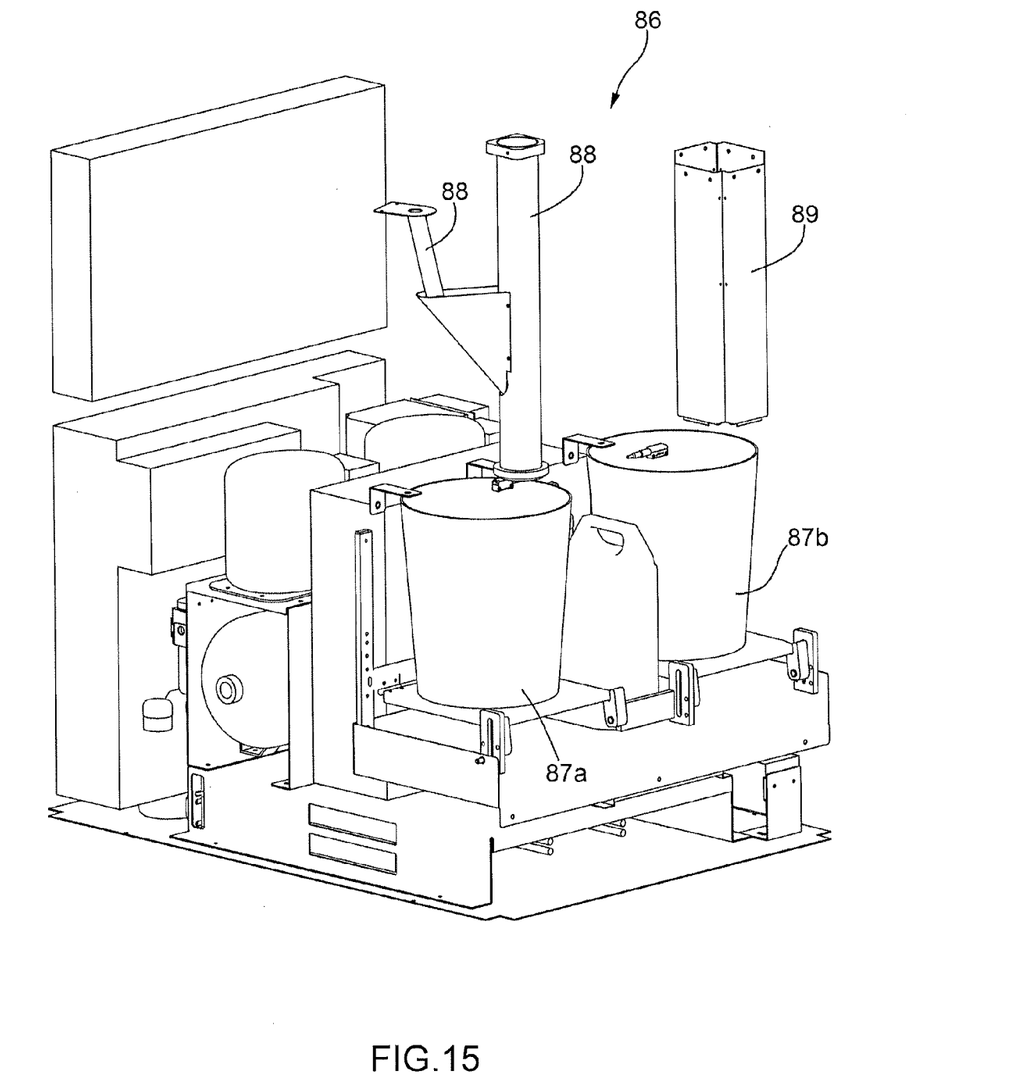
FIG. 15 is a diagrammatic perspective view, with parts removed for clarity, of a ninth detail of the machine in FIG. 1.

As shown in FIG. 15, the machine 1 is further provided with a collection device 86 of the processing waste (e.g. syringes 5, bottle 7, needles 78, and caps 85) accommodated within the frame 2 underneath the store 8, and comprising, in the case in point, two collection containers 87, of which one (hereinafter indicated by numeral 87a) communicates with the chamber 3 by means of a pair of chutes 88 and the other (hereinafter indicated by numeral 87b) communicates with the chamber 3 itself by means of one chute 89 only.

In use, the various processing waste is selectively fed by the device 10 to the various chutes 88, 89 and, thus, to the various containers 87a, 87b, thus allowing to separate the processing waste.

The operation of the machine 1 is easily inferred from the description above and no further explanations are required.

The invention claimed is:

1. A machine for the preparation of pharmaceutical products, comprising:

at least one store for storing syringes, bottles, or a combination of syringes and bottles, the at least one store including a pocket conveyor mobile along a loop-shaped path, the pocket conveyor including a plurality of pockets and a pair of reciprocally parallel conveying belts or chains, each of the plurality of pockets extending between the conveying belts or chains and being rotationally coupled to each of the conveying belts or chains to oscillate with respect to the conveying belts or chains about a substantially horizontal fulcrum axis, and each of the plurality of pockets is configured to receive and hold a respective syringe or a respective bottle, each of the plurality of pockets including a first slot and a second slot;

a dosing station for transferring at least one pharmaceutical from a syringe to a bottle; and a gripping and transporting device that includes a pair of gripping jaws for transferring the syringes or the bottles between the store and the dosing station;

wherein the first slot is configured to engage a flange of a respective syringe to guarantee a correct axial positioning of the respective syringe and the second slot is configured receive the pair of gripping jaws therein during the process of removing a respective syringe or a respective bottle from the pocket.

2. A machine according to claim 1, wherein said loop-shaped path extends through a loading station of the syringes or of the bottles in the respective pockets and a picking station, at which the syringes or the bottles are picked from the respective pockets by means of said gripping and transporting device.

3. A machine according to claim 1, wherein each of the plurality of pockets has a longitudinal axis substantially parallel to said fulcrum axis.

4. A machine according to claim 1, wherein each of the plurality of pockets has a longitudinal axis arranged according to an angle other than zero with respect to said fulcrum axis.

5. A machine according to claim 1, wherein each of the plurality of pockets has a substantially V-shaped transversal section.

* * * * *